(12) United States Patent
Zarins

(10) Patent No.: US 10,722,625 B2
(45) Date of Patent: Jul. 28, 2020

(54) CORKSCREW SHAPE FOR RIGHT-SIDED CARDIAC DEVICE

(71) Applicant: Abiomed, Inc., Danvers, MA (US)

(72) Inventor: Christopher Zarins, Boston, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 15/156,570

(22) Filed: May 17, 2016

(65) Prior Publication Data

US 2017/0333607 A1 Nov. 23, 2017

(51) Int. Cl.
*A61M 1/10* (2006.01)
*A61M 1/12* (2006.01)

(52) U.S. Cl.
CPC .......... *A61M 1/1008* (2014.02); *A61M 1/102* (2014.02); *A61M 1/1086* (2013.01); *A61M 1/125* (2014.02); *A61M 2205/3331* (2013.01)

(58) Field of Classification Search
None
See application file for complete search history.

(56) References Cited

U.S. PATENT DOCUMENTS

| | | |
|---|---|---|
| 4,985,014 A | 1/1991 | Orejola |
| 6,395,026 B1 | 5/2002 | Aboul-Hosn et al. |
| 6,532,964 B2 | 3/2003 | Aboul-Hosn et al. |
| 6,544,216 B1 | 4/2003 | Sammler et al. |
| 6,726,696 B1 | 4/2004 | Houser et al. |
| 6,974,436 B1 | 12/2005 | Aboul-Hosn et al. |
| 7,022,100 B1 | 4/2006 | Aboul-Hosn et al. |
| 7,381,179 B2 | 6/2008 | Aboul-Hosn et al. |
| 7,445,592 B2* | 11/2008 | Pecor ................ A61M 5/14276 600/16 |
| 8,888,728 B2 | 11/2014 | Aboul-Hosn et al. |
| 8,992,406 B2 | 3/2015 | Corbett |
| 9,327,068 B2 | 5/2016 | Aboul-Hosn et al. |
| 9,545,468 B2 | 1/2017 | Aboul-Hosn et al. |

(Continued)

FOREIGN PATENT DOCUMENTS

| | | |
|---|---|---|
| EP | 0916359 A1 | 5/1999 |
| EP | 1082150 | 3/2001 |

(Continued)

OTHER PUBLICATIONS

Australian Examination Report for Australian Application Serial No. 2012261630, dated Jan. 21, 2014.

(Continued)

*Primary Examiner* — Ankit D Tejani
(74) *Attorney, Agent, or Firm* — Botos Churchill IP Law LLP

(57) ABSTRACT

A catheter includes a catheter body, a pump assembly and a cannula. The pump assembly can be disposed at a distal end of the catheter body and has a distal portion. The cannula can be coupled to the distal end portion of the pump assembly and can include a proximal cannula portion and a distal cannula portion. The distal cannula portion has an approximately helical shape which can allow the cannula to be inserted into a patient's right heart and pump blood therethrough. In certain implementations, the distal tip of the helical shape has a slight bias relative to the main helix to further facilitate delivery of the device. In certain applications this bias is toward the central axis of the helix.

19 Claims, 8 Drawing Sheets

(56) References Cited

U.S. PATENT DOCUMENTS

| | | |
|---|---|---|
| 9,561,314 B2 | 2/2017 | Aboul-Hosn et al. |
| 9,597,437 B2 | 3/2017 | Aboul-Hosn et al. |
| 9,814,813 B2 | 11/2017 | Corbett |
| 2002/0026944 A1 | 3/2002 | Aboul-Hosn et al. |
| 2002/0045795 A1 | 4/2002 | Aboul-Hosn et al. |
| 2005/0228212 A1* | 10/2005 | Aboul-Hosn ............. A61F 2/82 600/16 |
| 2005/0234288 A1 | 10/2005 | Aboul-Hosn et al. |
| 2008/0008688 A1* | 1/2008 | Stokes ............... A61K 38/1709 424/93.21 |
| 2009/0005725 A1 | 1/2009 | Shorey |
| 2010/0087773 A1 | 4/2010 | Ferrari |
| 2012/0203056 A1 | 8/2012 | Corbett |
| 2015/0073202 A1* | 3/2015 | Aboul-Hosn ......... A61M 1/125 600/16 |
| 2015/0230921 A1* | 8/2015 | Chau .................... A61F 2/2418 623/2.11 |
| 2015/0328459 A1* | 11/2015 | Chin .................... A61N 1/3756 607/21 |
| 2016/0045651 A1 | 2/2016 | Corbett |

FOREIGN PATENT DOCUMENTS

| | | |
|---|---|---|
| JP | 2002514472 A | 5/2002 |
| JP | 2002515301 A | 5/2002 |
| WO | WO-1999/002204 | 1/1999 |
| WO | WO-9958170 A1 | 11/1999 |
| WO | WO-1999059652 A1 | 11/1999 |
| WO | WO-2005037345 A2 | 4/2005 |
| WO | WO-2010010407 A1 | 1/2010 |

OTHER PUBLICATIONS

Drummond, et al., "Three-Dimensional Birtual Anatomic Fit Study for an Implantable Periatric Ventricular Assist Device", Computational Science ICCS 2006 Lecture Notes in Computer Science, 3994:855-861 (2006).

European Examination Report for EPO Application Serial No. 11725255.1, dated Jul. 10, 2014.

European Search Report issued in EP App. 16 17 0029 dated Aug. 25, 2016.

PCT International Preliminary Report on Patentability for PCT/US/2011037984, dated Dec. 6, 2012 (9 pages).

PCT International Search Report for PCT/US2011/037984, dated Sep. 9, 2011 (6 pages).

* cited by examiner

CORKSCREW SHAPE FOR RIGHT-SIDED CARDIAC DEVICE

BACKGROUND

A ventricular assist device (VAD), such as a percutaneous intracardiac heart pump assembly, can be introduced in the heart to deliver blood from the heart into an artery. VADs are designed to assist either the right or left ventricle or both at once. When deployed in the heart, a VAD can pull blood from one chamber of the heart and expel it into the aorta or pulmonary artery to facilitate the flow of blood through the heart and throughout the body. In one common approach, VADs are inserted by a catheterization procedure through the femoral artery into the left heart of a patient, or through the femoral vein into the right heart of the patient.

VADs designed for right heart assistance (RVADs) can extend through the pulmonary valve and into the pulmonary artery in order to expel blood into the pulmonary artery. To properly position certain RVADs, the devices must be passed through the inferior vena cava, right atrium, tricuspid valve, right ventricle and finally the pulmonary valve. The stiffness of these RVADs typically must be higher than the stiffness of other cardiac devices (e.g., Swan-Ganz catheters) which are typically smaller and are not designed to prevent displacement due to the force of fluid flow. While the higher stiffness of the RVAD enables long-term use of the device, it may also increase the difficulty of inserting the RVAD. This difficulty is exacerbated in the case of patients with abnormal right heart anatomies because RVADs may be designed based on a mean patient population. In these cases, the relatively stiff cannula of the RVAD can interfere with positioning the device in the pulmonary artery after the device passes through the tricuspid valve. Accordingly, some medical practitioners may experience difficulties in placing the RVAD in certain patients, particularly at the stage of advancing the RVAD through the tricuspid valve toward the pulmonary artery.

SUMMARY

Systems, methods, and devices for a VAD shaped to improve delivery of the VAD into the right heart are presented herein. The VAD includes a cannula having an approximately helical shape. The helical shape facilitates the advancement of the cannula into and/or through the right ventricle. In particular, the shape may facilitate advancement through the tricuspid and/or pulmonary valves. The shape of the cannula facilitates or enables the advancing of the device into the heart using a twisting, rotating, or screw motion. Such a motion can allow the cannula to more easily proceed through the patient's anatomy and particularly through the tricuspid valve and toward the pulmonary artery. The distal tip of the helical cannula can also be shaped to facilitate this motion. The tip may be angled toward the axis of the cannula's helical shape and may thus have a tighter curvature than the remainder of the cannula, such that the distal tip is oriented in a favorable direction during device delivery. The shape of the cannula can mimic the internal anatomy of the pathway that the device takes through the heart so that correct positioning of the device is achieved in the majority of patients without difficulty.

The helical shape of the cannula can be determined from analysis of medical images of patient right heart anatomies. The average right heart anatomy of the areas in which the cannula is to be positioned and through which the cannula passes may possess a somewhat helical shape. Therefore, pairing a cannula's helical shape with the shape of the right heart anatomy can allow the cannula to move through the heart anatomy more easily than a cannula lacking a helical shape matching the anatomy. In some implementations, the VAD, when positioned in the right heart, has an outflow port positioned distal to the pulmonary valve and an inflow port located in the inferior vena cava. The cannula of the VAD can traverse the inferior vena cava, right atrium, tricuspid valve, right ventricle, and pulmonary valve.

In one aspect, a catheter comprises a catheter body, a pump assembly, and a cannula. The catheter body has a distal end, a proximal end, and a longitudinal axis. The pump assembly is disposed at the distal end of the catheter body and has a distal portion. The cannula is coupled to the distal end portion of the pump assembly. The cannula comprises a proximal cannula portion and a distal cannula portion. The distal cannula portion has an approximately helical shape. In certain implementations, the helical shape approximated by the distal cannula portion has an axis parallel to the longitudinal axis of the catheter body. In some implementations, the distal tip of the cannula is angled toward a center of the helical shape axis.

In some implementations, the helical shape approximated by the distal cannula portion has a radius between about 10 mm and 50 mm. In certain implementations, the helical shape approximated by the distal cannula portion has a radius between about 20 mm and 40 mm. In some implementations, the helical shape approximated by the distal cannula portion has a radius of about 30 mm. In certain implementations, the helical shape approximated by the distal cannula portion has a pitch between about 50 mm and 140 mm. In some implementations, the helical shape approximated by the distal cannula portion has a pitch between about 70 mm and 120 mm. In certain implementations, the helical shape approximated by the distal cannula portion has a pitch of about 90 mm. In some implementations, the helix completes one turn. In some implementations, the length of the distal cannula portion is about two-thirds of a total length of the cannula. In certain implementations, the total length of the cannula is about 17 cm.

In certain implementations, the cannula is configured to extend through the tricuspid valve and the pulmonary valve into the inferior vena cava when positioned in the right heart. In some implementations, the cannula is configured to be approximately perpendicular to a plane defined by the tricuspid valve during entry through the right atrium into the right ventricle. In certain implementations, the curvature of the distal end of the cannula is configured such that a distal tip of the cannula points toward the pulmonary valve after passing through the tricuspid valve.

In some implementations, the helical shape of the cannula is configured to match an average patient anatomy of the right atrium, tricuspid valve, right ventricle, pulmonary valve, and pulmonary artery during placement in the right heart. In certain implementations, the cannula is sized for percutaneous delivery. In some implementations, the cannula has a diameter of about 22 Fr. In certain implementations, the catheter further includes a flexible extension coupled to the distal cannula portion.

In another aspect, a heart pump assembly comprises a rotor, a housing, and a cannula. The housing is sized for percutaneous insertion and encloses the rotor. The housing has a distal end portion coupled to the cannula. The cannula comprises a proximal cannula portion and a distal cannula portion. The distal cannula portion has an approximately helical shape. In some implementations, the helical shape approximated by the distal cannula portion has an axis parallel to a longitudinal axis of the proximal cannula portion. In certain implementations, the helical shape approximated by the distal cannula portion has a diameter between about 20 mm and 40 mm. In some implementations, the helical shape approximated by the distal cannula portion has a pitch between about 70 mm and 120 mm. In certain implementations, a distal tip of the cannula is angled toward a center of the helical shape axis to ensure proper orientation while passing through the anatomy.

In another aspect, a method for placing a catheter in a patient's right heart includes advancing the catheter through a femoral vein to the inferior vena cava, simultaneously rotating and translating the helically-shaped distal tip through the tricuspid valve and into the right atrium in a screw-like motion, and advancing the helically-shaped distal tip through the pulmonary valve into the pulmonary artery. The catheter comprises a heart pump and a helically-shaped distal tip. In some implementations, the method further includes positioning the catheter across the pulmonary valve such that an outlet port is positioned in the pulmonary artery. In certain implementations, the method further includes positioning the catheter such that an inlet port is positioned in the inferior vena cava. In some implementations, advancing the catheter through the femoral vein comprises advancing the catheter over a guidewire.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices described herein, certain illustrative embodiments will be described. Implantable cannulas according to the embodiments and features described herein can be implanted with or without use of a guidewire. Although the embodiments and features described herein describe a cannula with a helical shape matched to an average heart anatomy of a percentage of a patient population, the cannula may be produced so as to fit a helix describing the anatomical structure of a single patient, in particular if the patient's heart anatomy differs from the average anatomy of the matched patient population, or if the patient is a child.

Systems, methods, and devices for a VAD shaped to improve delivery of the VAD into the right heart are presented herein. The VAD includes a cannula having an approximately helical shape. The helical shape facilitates the advancement of the cannula into and/or through the right ventricle. In particular, the shape may facilitate advancement through the tricuspid and/or pulmonary valves. The shape of the cannula facilitates or enables the advancing of the device into the heart using a twisting, rotating, or screw motion. Such a motion can allow the cannula to more easily proceed through the patient's anatomy and particularly through the pulmonary valve into the pulmonary artery. The distal tip of the helical cannula can also be shaped to facilitate this motion. The tip may be angled toward the axis of the cannula's helical shape and may thus have a tighter curvature than the remainder of the cannula. The shape of the cannula can mimic the internal anatomy of the pathway that the device takes through the heart so that correct positioning of the device is achieved in the majority of patients without difficulty.

The helical shape of the cannula was determined from analysis of medical images of patient right heart anatomies. The average right heart anatomy of the areas in which the cannula is to be positioned and through which the cannula passes may possess a somewhat helical shape. Therefore, pairing a cannula's helical shape with the shape of the right heart anatomy can allow the cannula to move through the heart anatomy more easily than a cannula lacking a helical shape matching the anatomy. In some implementations, the VAD, when positioned in the right heart, has an outflow port positioned distal to the pulmonary valve and an inflow port located in the inferior vena cava at the level of the diaphragm. The cannula of the VAD can traverse the inferior vena cava, right atrium, tricuspid valve, right ventricle, and pulmonary valve.

Figure 1:
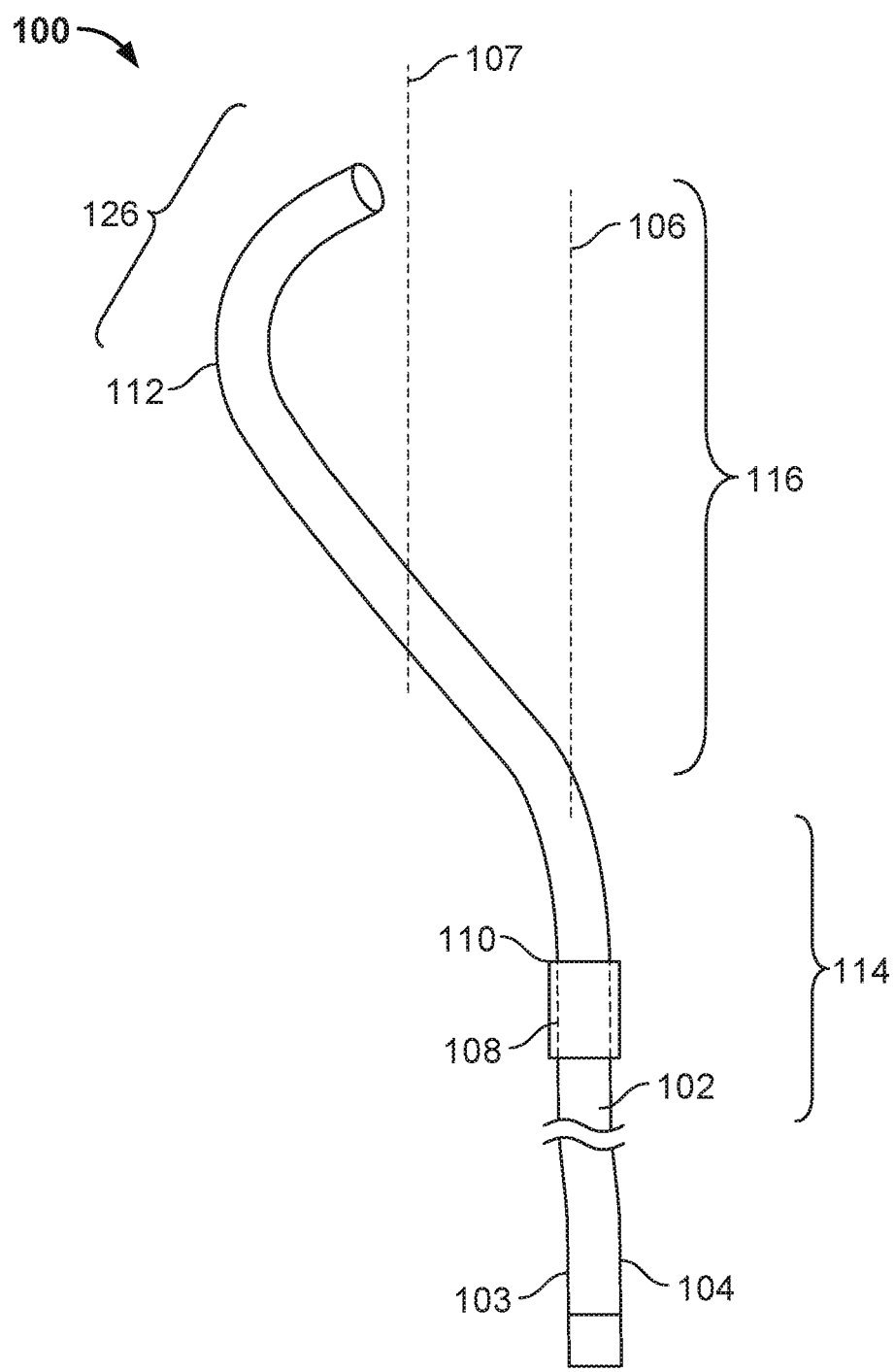
FIG. 1 shows a front view of a catheter including a cannula having a helical shape.

FIG. 1 shows a front view of a catheter 100 including a cannula 112 having a helical shape according to certain implementations. The catheter 100 includes a catheter body 103, a pump assembly 108, and a cannula 112 having a pre-formed helical shape. The catheter body 103 has a distal end 102, a proximal end 104, and a longitudinal axis 106. The pump assembly 108 is coupled to the distal end 102 of the catheter body 103. The cannula 112 is coupled to a distal end portion 110 of the pump assembly 108. The cannula 112 has a proximal cannula portion 114 and a distal cannula portion 116. The distal cannula portion 116 has an approximately helical shape. The approximately helical shape has a central axis 107 which is substantially parallel to the longitudinal axis 106. The proximal cannula portion 114 may be approximately parallel to the longitudinal axis 106 of the catheter body 103 and may be approximately straight.

The helically-shaped distal cannula portion 116 includes a partial rotation about the central axis 107. The helical shape of the distal cannula portion 116 may approximate the anatomy of the right heart, allowing the catheter 100 to be inserted into the right heart of a patient with a screw-like motion. A distal tip 126 of the distal cannula portion 116 may deviate from the helical shape in order to further approximate the right heart anatomy. For example, the distal tip 126 may be angled toward the central axis 107 i.e., having a greater curvature relative to the remainder of the distal cannula portion 116. In certain implementations, the distal tip 126 may have less of a curvature relative to the remainder of the distal cannula portion 116. In certain implementations, the distal tip 126 of the cannula 112 may narrow toward the distal tip 126 of the distal cannula portion 116, which can further facilitate passage through the heart valves. In certain implementations, a flexible extension can be connected to the distal tip 126 to prevent traumatic contact of the distal tip 126 with interior walls of the heart following insertion.

The catheter 100 can be advanced into the right heart in the following manner. First, the distal tip 126 of the cannula 112 is advanced through the inferior vena cava into the pulmonary artery. Next, the catheter 100 may be rotated (e.g., clockwise) and advanced in a screw motion through the tricuspid valve toward the pulmonary artery. Then, the screw motion may be repeated to advance the distal tip 126 through the pulmonary valve into the pulmonary artery. When the distal tip 126 of the cannula 112 is positioned within the pulmonary artery, the pump assembly 108 may remain in the inferior vena cava. The pump 108 may be activated once this position is achieved to pump blood from the inferior vena cava into the pulmonary artery. Thus, by enabling the advancing of the cannula 112 by a screw motion, the shape of the distal cannula portion 116 facilitates correct positioning of the catheter 100 in the right heart.

Figure 2A:
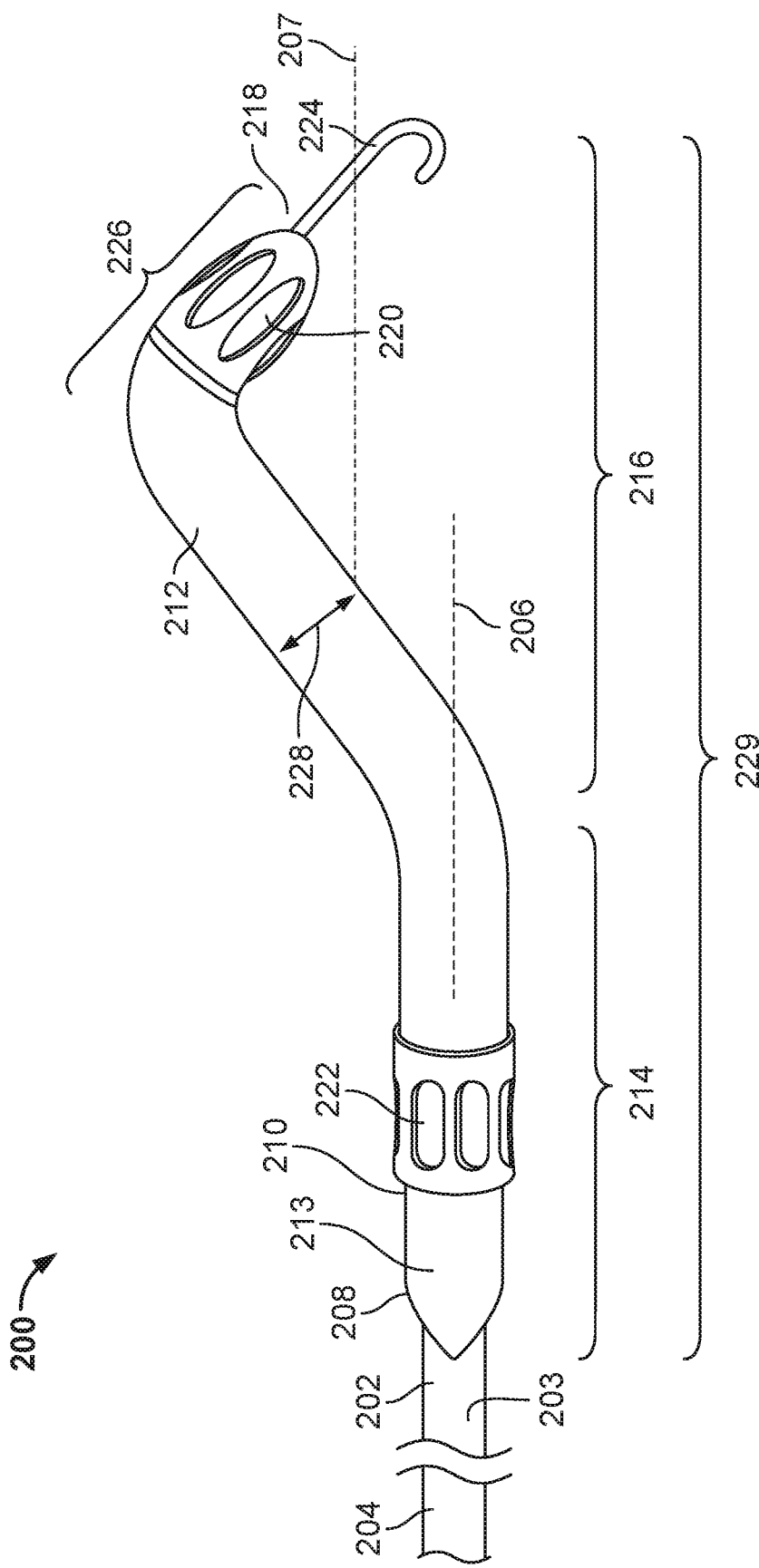
FIG. 2A and FIG. 2B show a detailed view of a catheter including a cannula having a helical shape for right heart insertion.
Figure 2B:
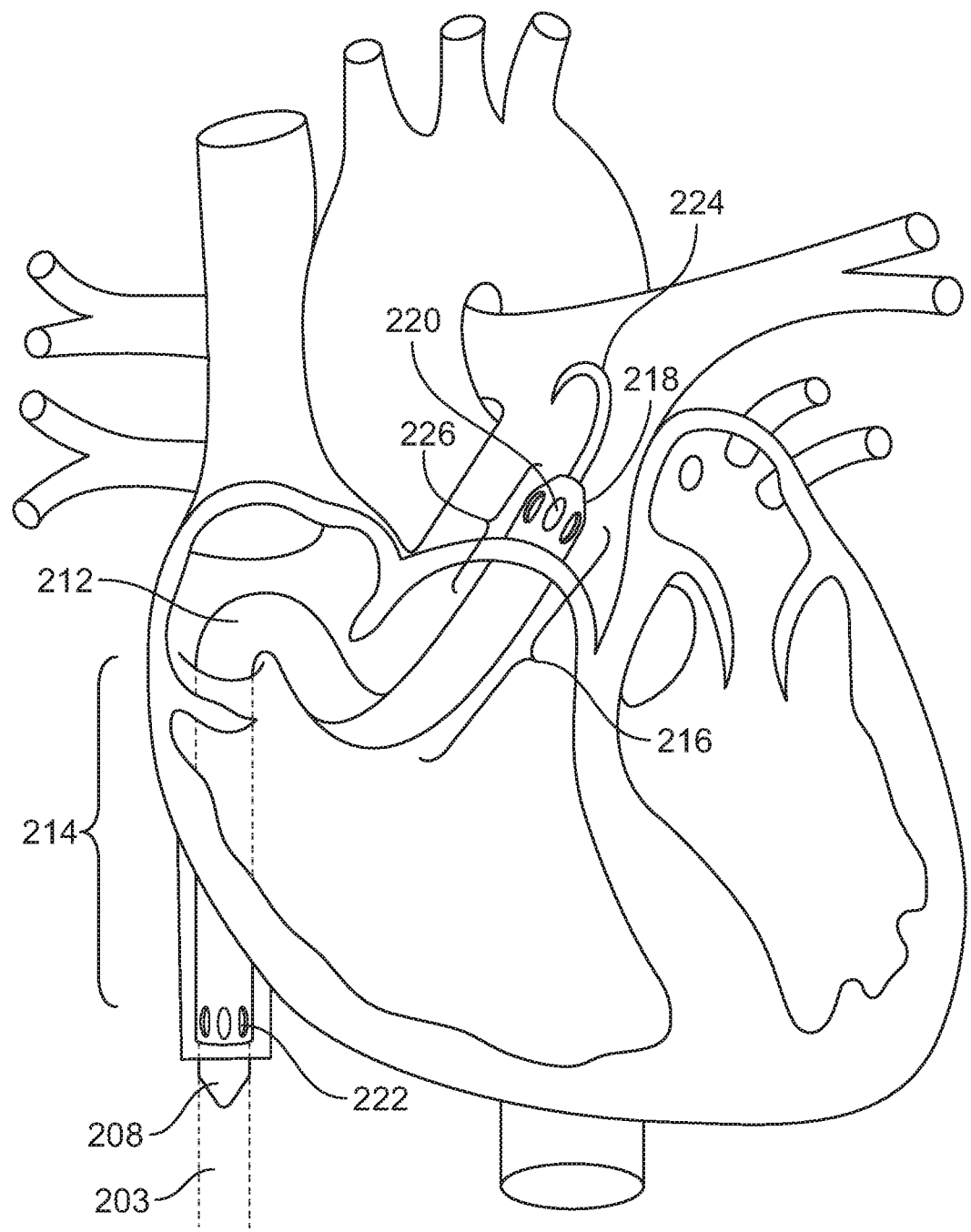

FIG. 2A and FIG. 2B show a detailed view of catheter 200 having a cannula with a helical shape for insertion into the right heart according to certain implementations. The catheter 200 includes a catheter body 203, a pump assembly 208, and a cannula 212. The catheter body 203 includes a proximal end 204 and a distal end 202. The distal end 202 of the catheter body 203 is coupled to the pump assembly 208. The cannula 212 is coupled to a distal end portion 210 of the pump assembly 208. The cannula 212 includes a substantially straight proximal cannula portion 214, a substantially helical distal cannula portion 216, a distal tip 226, a distal end 218, inlet ports 222, outlet ports 220, and a flexible projection 224.

The cannula 212 is sized to be positioned such that the cannula 212 traverses the inferior vena cava, right atrium, tricuspid valve, right ventricle and pulmonary valve of the heart. This allows the inlet ports 222 to be positioned in the inferior vena cava when the outlet ports 220 are positioned in the pulmonary artery. In some implementations, the length 229 of the cannula 212 is 17 cm. In certain implementations, the length 229 of the cannula is 10 cm, 12, cm, 15 cm, 17 cm, 18 cm, 20 cm or any other suitable length. The cannula 212 is constructed to allow fluid to flow into the inlet ports 222, through the cannula 212, and out the outlet ports 220. The fluid may be propelled through the cannula 212 by a rotor located in the pump assembly 208. The cannula 212 may be configured to be relatively stiff in order to increase the stability of the cannula 212 once in place in the right heart. The curvature of the cannula 212 may reduce the need for flexibility of the cannula 212 during insertion.

The cannula 212 is also sized for passage through a femoral artery and other vasculature of a patient. In some implementations, the cannula 212 has a cannula diameter 228 of about 22 Fr. In certain implementations, the cannula 212 has a cannula diameter 228 of 7 Fr, 8 Fr, 10 Fr, 11 Fr, 12 Fr, 18 Fr, 20 Fr, 24 Fr, or any other suitable diameter. The cannula diameter 228 may be approximately constant along the length 229 of the cannula 212.

The distal portion 216 of the cannula 212 helps the cannula 212 to be positioned within the right heart of a patient. The helical shape of the distal cannula portion 216 allows the cannula 212 to be dynamically positioned in the right heart using a screw-like rotation motion that follows the anatomy of the right heart. The distal cannula portion 216 may have a curvature that mimics the anatomical pathway of the cannula 212 during positioning in the right heart. In some implementations, the distal cannula portion 216 has a length of about two-thirds of the total length 229 of the cannula 212.

The distal tip 226 of the cannula 212 further facilitates insertion of the cannula 212. The distal tip 226 may deviate from the helix approximating the shape of the remainder of the distal cannula portion 216. In particular, the distal tip 226 of the cannula 212 may have either a greater or lesser curvature than the remainder of the distal cannula portion 216. The curvature of the distal tip 226 causes the distal tip 226 to be oriented toward the tricuspid valve during initial insertion of the cannula 212 into the right atrium. This facilitates insertion because, once in the right atrium, the cannula 212 must make a relatively tight turn toward the tricuspid valve to enter the right ventricle. The shape of the distal tip 226 also causes the distal tip 226 to be oriented toward the pulmonary valve upon entry into the right ventricle. This facilitates insertion because, once in the right ventricle, the cannula 212 must be oriented toward the pulmonary valve to enter the pulmonary artery. In some implementations, the distal tip 226 of the cannula 212 narrows toward the distal end 218 of the distal cannula portion 216, which can further facilitate passage through the heart valves.

Additionally, the flexible extension 224 is connected to the distal end 218 of the distal tip 226 to help prevent traumatic contact with the interior walls of the heart after insertion of the cannula 212 into the heart. The flexible projection 224 may be formed as a pigtail, a ball, a flexible rod, or as any other suitable extension from the distal end of the cannula portion 218. In some implementations, the flexible projection 224 mechanically, but not hydraulically, extends the cannula 212. The flexible projection 224 may prevent the cannula 212 from traumatically engaging with heart tissue. In certain implementations, the distal tip 226 does not include the flexible projection 224.

The pump assembly 208 may contain a rotor (not shown) which may be driven by an implantable or external drive unit. The pump assembly 208 comprises a housing 213 which may be comprised of a different material than the cannula 212 or catheter 203. The rotor of the pump assembly 208 may be located in the housing 213 and attached to a drive shaft. Although an embodiment with an implantable motor is shown in FIG. 2A, in some implementations the unit driving the drive shaft is located external to the patient's body and the drive shaft extends through the catheter body 203. In some implementations, a motor driving the drive shaft is enclosed within the pump assembly 208. Any suitable pump and/or drive known in the art may be used.

The pump assembly 208 is configured to provide a fluid flow into the cannula 212 at the inlet ports 222, through the cannula 212, and out the outlet ports 220. The pump assembly 208 may be configured to provide a flow rate of 4 liters per minute (lpm 0 or more within the right heart of a patient. In some implementations, the pump assembly 208 provides a flow rate of 3 lpm, 3.5 lpm, 4 lpm, 4.5 lpm 5 lpm, 6 lpm or any other suitable flow rate. In some implementations, the flow rate is chosen based on the needs of the patient.

Figure 3:
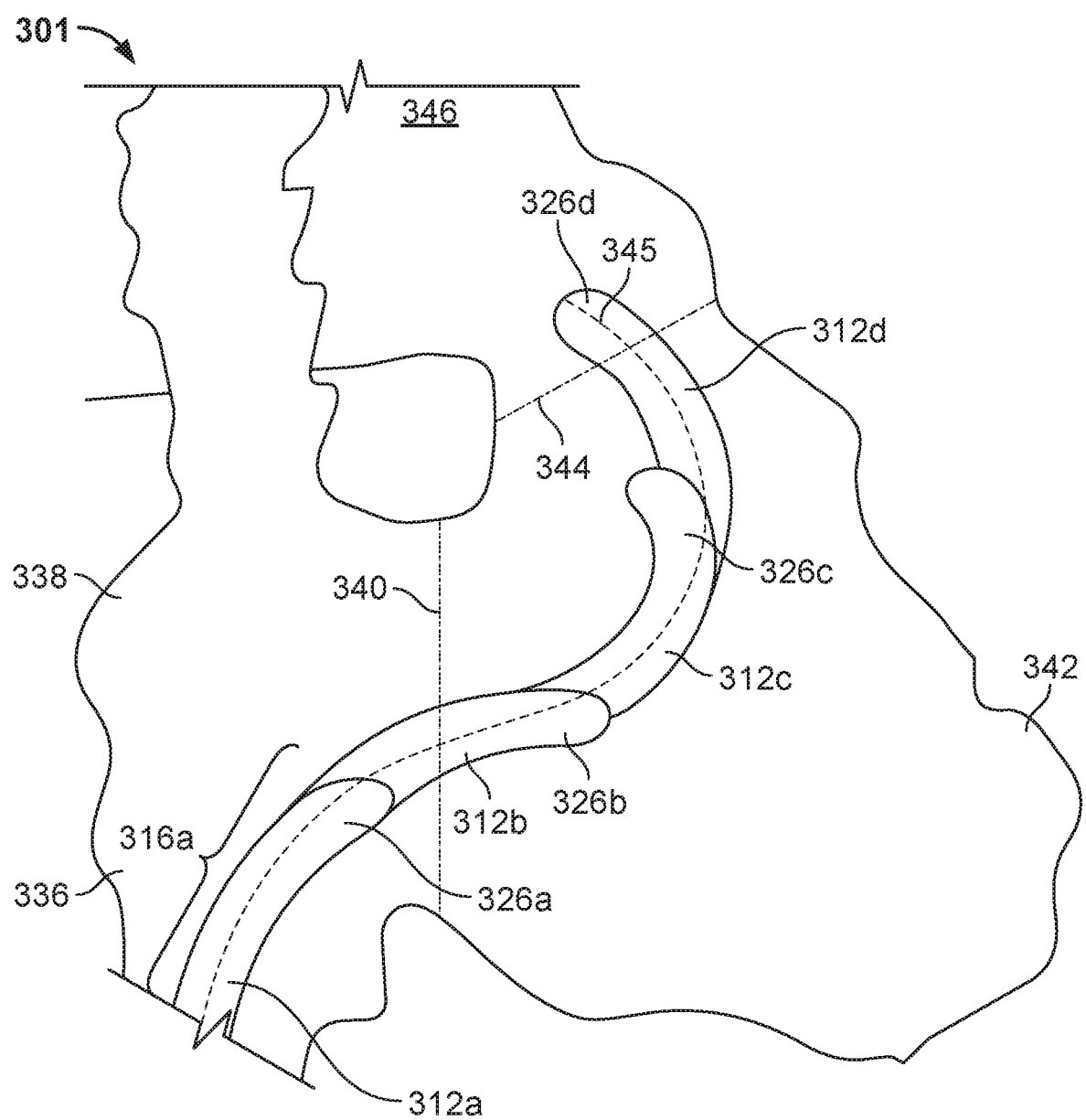
FIG. 3 shows an illustrative view of multiple overlays of the cannula at various positions during insertion into the right heart.

FIG. 3 shows a cannula 312 in four successive positions 312a-312d during insertion into the heart 301 according to certain implementations. The heart includes an inferior vena cava 336, a right atrium 338, a tricuspid valve 340, a right ventricle 342, a pulmonary valve 344, and a pulmonary artery 346. The cannula 312 includes a distal cannula portion 316, and a distal tip 326. The cannula 312 follows an approximately helical trajectory 345 from position 312a to 312d as it is inserted into the heart 301. The distal tip 326 leads the cannula 312 along the helical trajectory 345.

The first position 312a shows the cannula after it has been introduced through the inferior vena cava 336 into the right atrium 338 of the patient. The distal tip 326a of the cannula 312a is oriented such that the distal tip 326a is pointed toward the tricuspid valve 340. The distal tip 326 of the cannula 312 deviates slightly from the helical trajectory 345 because the distal tip 326 is angled toward a central axis of the helical shape formed by the distal cannula portion 316. In some implementations, the cannula 312 is inserted into the right heart 301 over a guidewire. In certain implementations, a flexible projection is attached to the distal end of the cannula 312 which prevents traumatic contact of the cannula 312 with the interior walls of the heart 301 by providing a flexible extension of the cannula 312. In some implementations, a flexible extension is straight during insertion and is curved upon removal of a guidewire after insertion.

The second position 312b shows the cannula 312 after it has been advanced in a screw motion through the tricuspid valve 340 into the right ventricle 342. The cannula 312 in position 312b is approximately perpendicular to a plane defined by the tricuspid valve 340 and is positioned to advance the cannula 312 from the inferior vena cava 336 through the tricuspid valve 340 and then from the right ventricle 342 through the pulmonary valve 344 to the pulmonary artery 346.

The third position 312c shows the cannula 312 just before passage through the pulmonary valve 344. The catheter advances from the second position 312b to the third position 312c in a screw-like motion along the helical trajectory 345. This motion advantageously orients the distal tip 326c towards the pulmonary valve 344.

The fourth position 312d shows the cannula 312 after the cannula has been advanced through the pulmonary valve 344 into the pulmonary artery 346. The catheter advances from the third position 312c to the fourth position 312d in a screw-like motion along the helical trajectory 345. Once the cannula 312 is positioned in the fourth position 312d, pump operation may be initiated to pump blood from the inferior vena cava 336 to the pulmonary artery 346.

As shown by the illustrative positions 312a-d, the helical shape of the cannula 312 allows a screw motion to be used to rotate and translate the cannula 312 through the right heart of a patient. In some implementations, the cannula 312 is advanced into position over a guidewire or through a sheath. The cannula 312 may be configured for short-term use, such as during an emergency procedure or in conjunction with an imaging procedure. In some implementations, the cannula 312 may be configured for long-term use as a fully implantable heart pump. The cannula 312 may be used for long-term implantation in a patient (e.g., >1 hr, >3 hr, >6 hr, >12 hr, >24 hr, >2 days, >10 days, >20 days, >45 days, >60 days or any suitable duration). The cannula 312 may be inserted into the patient's vasculature surgically or percutaneously.

Figure 5:
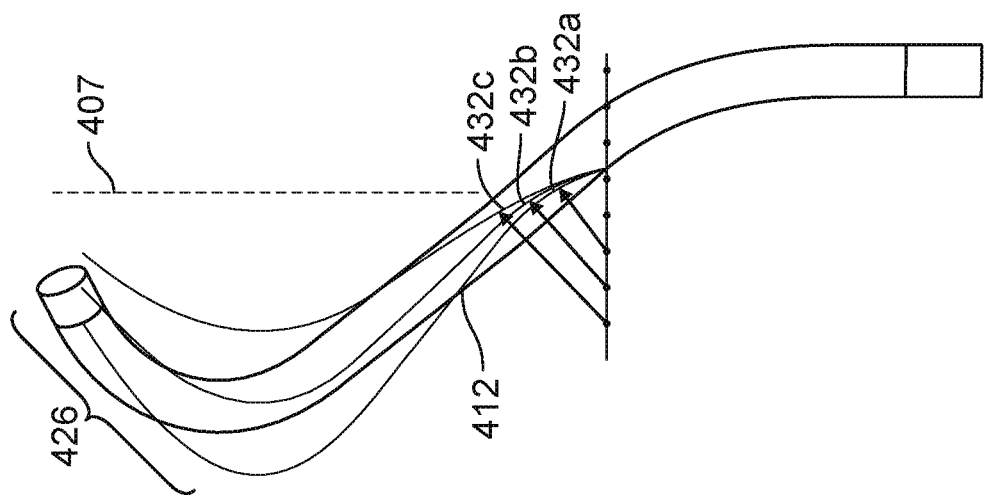
FIG. 5 shows a front view of a cannula having a helical shape characterized by a diameter.
Figure 4:
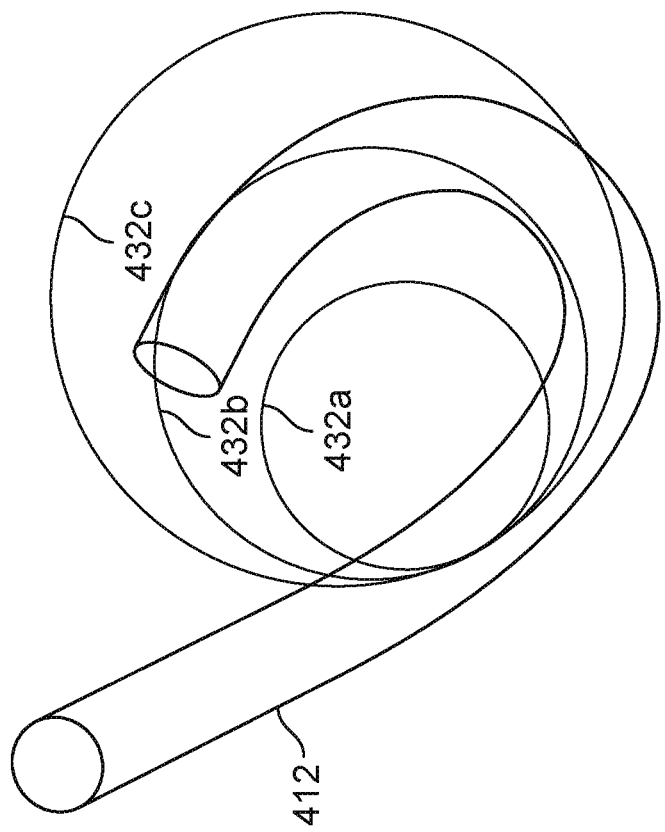
FIG. 4 shows a top view of a cannula having a helical shape characterized by a diameter.

FIG. 4 shows a top view of a cannula 412 according to certain implementations having a helical shape characterized by a diameter 432, and FIG. 5 shows a front view of the cannula 412. The curve of the cannula 412 may be approximated by helices 432 a-c of varying diameters. The cannula 412 is approximated by a helix 432b with a diameter of about 30 mm. In some implementations, the helix 432 has a diameter of about 10 mm, 20 mm, 30 mm, 40 mm, 50 mm, or any other suitable diameter. The diameter of helix 432b may approximate an average right heart anatomy of a patient population. Toward its proximal portion, the cannula 412 is more closely approximated by the helix 432c which has a relatively large diameter (e.g., 40 mm). Toward its distal tip 426, the cannula 412 is more closely approximated by the helix 432a which has a relatively small diameter (e.g., 20 mm). In some implementations, the cannula 412 may be approximately described by a uniform helix. In some implementations, the distal tip 426 of the cannula 412 may be oriented in a different direction than the main helix 407 to facilitate passage through the anatomy. In some implementations, the distal tip 426 of the cannula 412 may deviate from the helix by angling toward a center axis of the helix 407. In some implementations, the helical shape approximated by the cannula 412 may include a full turn. In some implementations, the helical shape approximated by the cannula 412 may include less than one full turn. In some implementations, the helical shape approximated by the cannula 412 may complete a turn of 180°, 200°, 220°, 240°, 260°, 280°, 300°, 330°, 360° or any other suitable turn.

Figure 7:
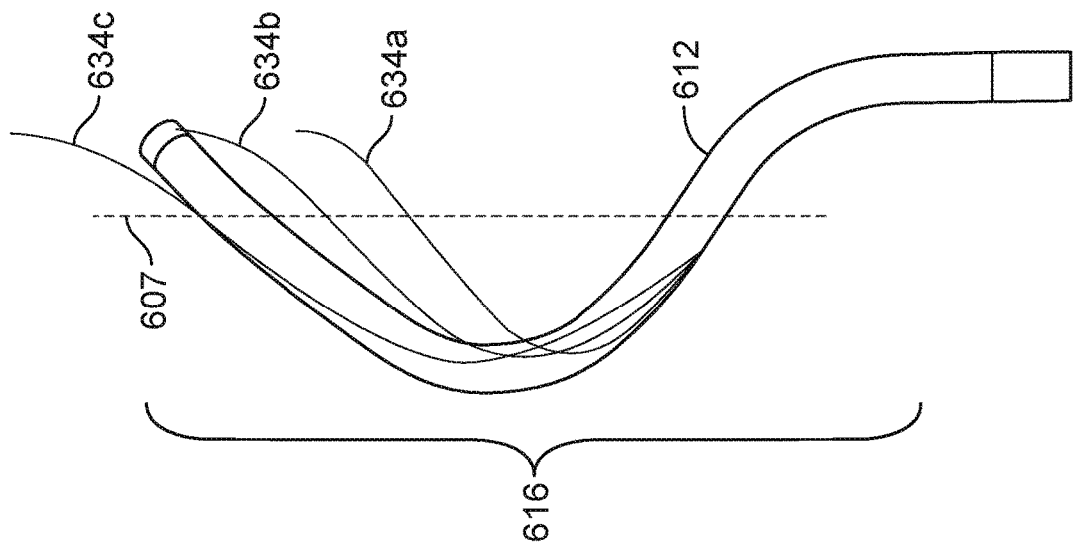
FIG. 7 shows a side view of a cannula having a helical shape characterized by a pitch.
Figure 6:
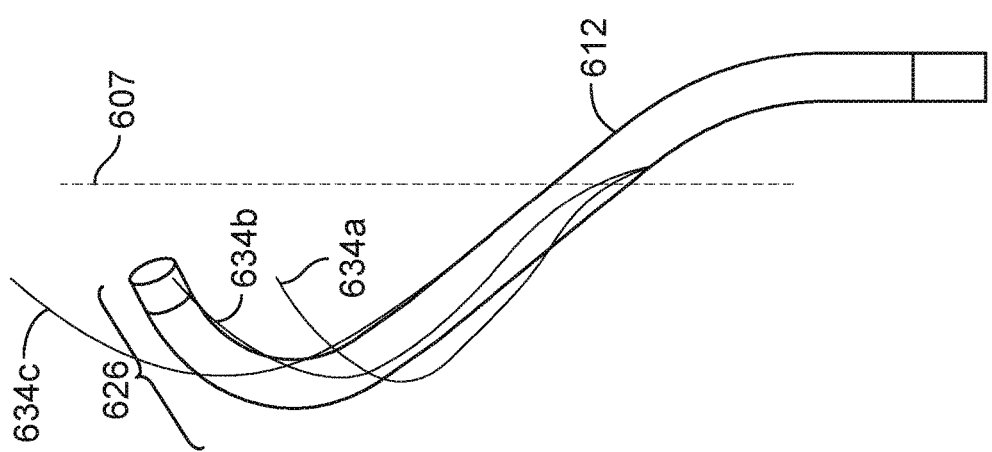
FIG. 6 shows a front view of a cannula having a helical shape characterized by a pitch.

FIG. 6 shows a front view of a cannula 612 according to certain implementations having a helical shape characterized by a pitch 634, and FIG. 7 shows a side view of the cannula 612. The curve of the cannula 612 may be approximated by helices 634 a-c of varying pitches. In a preferred implementation, the shape of the cannula 612 is approximated by a helix 634b with a pitch of about 90 mm. In some implementations, the helix 634 has a pitch of about 50 mm, 60 mm, 70 mm, 80 mm, 90 mm, 100 mm, 110 mm, 120 mm, 130 mm, 140 mm, 150 mm, or any other suitable pitch. The cannula 612 may be approximated by a helix 634b with a relatively low pitch (e.g., 70 mm) at a proximal end of the distal cannula portion 616, and may be better approximated by a different helix 634a with a relatively high pitch (e.g., 120 mm) at the distal end 626. The distal tip 626 may deviate from the pitch of the helix 634 which approximates the shape of the distal cannula portion 616. The distal tip 626 of the cannula 612 may angle in toward a center axis 607 of the helix.

The helix 634 may have a pitch such that the cannula 612 may be inserted into position in the right heart using a screw motion. The screw motion positions the cannula 612, and in particular the distal tip 626 of the cannula 612, during insertion such that the distal tip 626 of the cannula 612 passes through the tricuspid valve, the right ventricle and pulmonary valve and into the pulmonary artery. The cannula 612 body follows the distal tip 626 through the anatomy of the heart along the helical pathway. The cannula 612 is positioned in the right heart without need for extensive repositioning.

Figure 8:
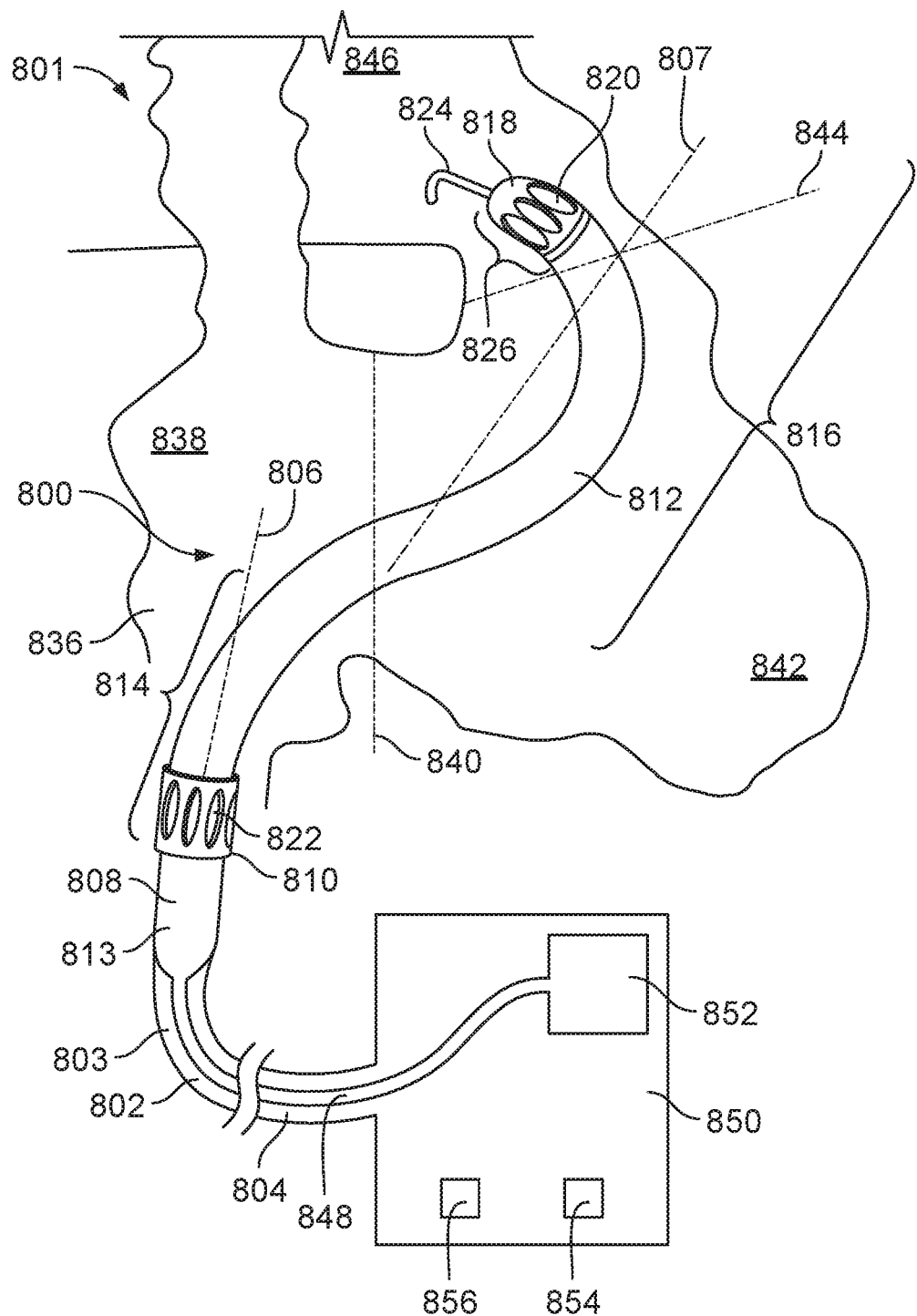
FIG. 8 shows a catheter including a cannula having a helical shape positioned in the right heart of a patient.

FIG. 8 shows a catheter 800 with a helical shape positioned in the right heart 801 of a patient according to certain implementations. The catheter 800 includes a catheter body 803, a pump assembly 808, a cannula 812, and a control unit 850. The catheter body 803 includes a catheter proximal end 804 and a catheter distal end 802. The control unit 850 is coupled to the catheter body 803 at the catheter proximal end 804. The pump assembly 808 is coupled to the catheter body 803 at the catheter distal end 802. The pump assembly 808 may include a housing 813 for a rotor. The cannula 812 is coupled to the pump assembly 808 at the distal end of the pump assembly 810. The cannula 812 comprises a proximal cannula portion 814 which is approximately straight along a longitudinal axis 806 of the catheter body 803. The cannula 812 further comprises a distal cannula portion 816 which approximates a helical shape fit to the interior anatomy of the right heart 801. The helical shape of the distal cannula portion 816 may have a curvature based on the anatomic path that the cannula 812 is designed to traverse. The cannula 812 includes inlet ports 822 located on the proximal cannula portion 814, and outlet ports 820 located at a distal tip 826 of the cannula 812. The distal tip 826 of the cannula 812 may be angled toward a toward a center axis of the helix 807 approximating the curvature of the distal cannula portion 816. The cannula 812 includes a flexible projection 824 coupled to the cannula 812 at the distal end of the cannula portion 818. The flexible projection 824 mechanically extends the cannula 812 such that the cannula 812 does not traumatically impact the interior walls of the heart after insertion and positioning. As will be appreciated, the catheter 800 need not include this flexible projection 824.

The cannula 812 may be percutaneously inserted or surgically implanted in the right heart of a patient. The cannula 812 can be placed in the right heart of a patient by insertion through a femoral artery and/or over a guidewire. The cannula 812 is inserted into the right heart 801 through the inferior vena cava 836 and right atrium 838, through the tricuspid valve 840 into the right ventricle 842 and finally through the pulmonary valve 844 and into the pulmonary artery 846. The cannula 812 can be advanced through the heart using a simple screw-like motion to rotate and translate the helically-shaped cannula 812 as described in FIG. 3. When in position, the cannula 812 traverses from the inferior vena cava 836 to the pulmonary artery 846. In some implementations, the cannula 812 extends into the pulmonary artery a distance of about 1 mm, 2 mm, 3 mm, 4 mm, 5 mm, 6 mm, 7 mm, 10 mm, 20 mm, 30 mm, 40 mm, 50 mm, 60 mm or any other suitable distance beyond the pulmonary valve. When in position in the right heart 801, the inlet ports 822 of the cannula 812 are located in the inferior vena cava 836 and the outlet ports 820 of the cannula 812 are located in the pulmonary artery 846. In some implementations, the outlet ports 820 of the cannula 812 are oriented such that the outflow is pointed in a downwards direction to facilitate the delivery of blood into the pulmonary artery 846 during operation.

During use, the rotor enclosed in the housing 813 of the pump assembly 808 creates a blood flow into the inlet ports 822 in the inferior vena cava 836. The blood flow traverses the interior of the cannula 812 and exits the cannula 812 at the outlet ports 820 at the distal tip 826 of the cannula. The blood exits the cannula 812 into the pulmonary artery 846, thus facilitating the blood flow from the inferior vena cava 836 and right atrium 838 into the pulmonary artery 846.

The rotor in the pump assembly 808 provides the flow of blood through the cannula 812. As previously mentioned, in some implementations, the rotor is driven by an implantable or external drive unit. In some implementations, the drive unit is located in an external unit such as the control unit 850. The pump assembly 808 may include a drive shaft (not shown) which is connected to the control unit 850. The control unit 850 may include controls 856, 854 for the operation of the pump assembly 808. For example, the control unit 850 may include a control 856 for the flow rate of the blood through the cannula 812. The flow rate of the blood through the cannula 812 can be controlled at the control unit 850 by adjusting the rate of rotation of a rotor. The pump assembly 808 also may include a purge system to prevent the ingress of blood into the pump assembly 808 and/or to cool and lubricate components of the pump assembly 808. The catheter body 803 may include a fluid supply line 848 to connect a purge system at the pump assembly 808 to a fluid supply reservoir 852 located in the external control unit 850. The purge system including the fluid supply reservoir 852 and fluid supply line 848 may provide purge fluid, lubricant, coolant, medicine, or any suitable hemocompatible fluid to the pump assembly 808. The control unit 850 may further include indications and/or warnings to an operator regarding operating conditions. In some implementations, the fluid supply reservoir 852 and fluid supply controls 854 are located in a separate control unit than the controls 856 for the catheter pump, rotor, and motor.

The cannula designs disclosed herein are designed with a shape derived from analysis of a representative sample of the patient population. The regions of overlap in a representative sample population may be used to determine the shape of the cannula. The shape of the cannula may be derived from the region of overlap between a significant proportion (86-96%) of the patient population. Further adaptations to the cannula design may be made based upon CT scans of a patient. In particular, if a CT scan of a patient shows that the right heart of the patient is anomalous, such as larger, smaller or differently shaped than a majority of the population, the helical shape of the cannula may be altered or the helix approximating the cannula may be chosen so as to fit the right heart anatomy of the patient determined from the CT scan.

Figure 9:
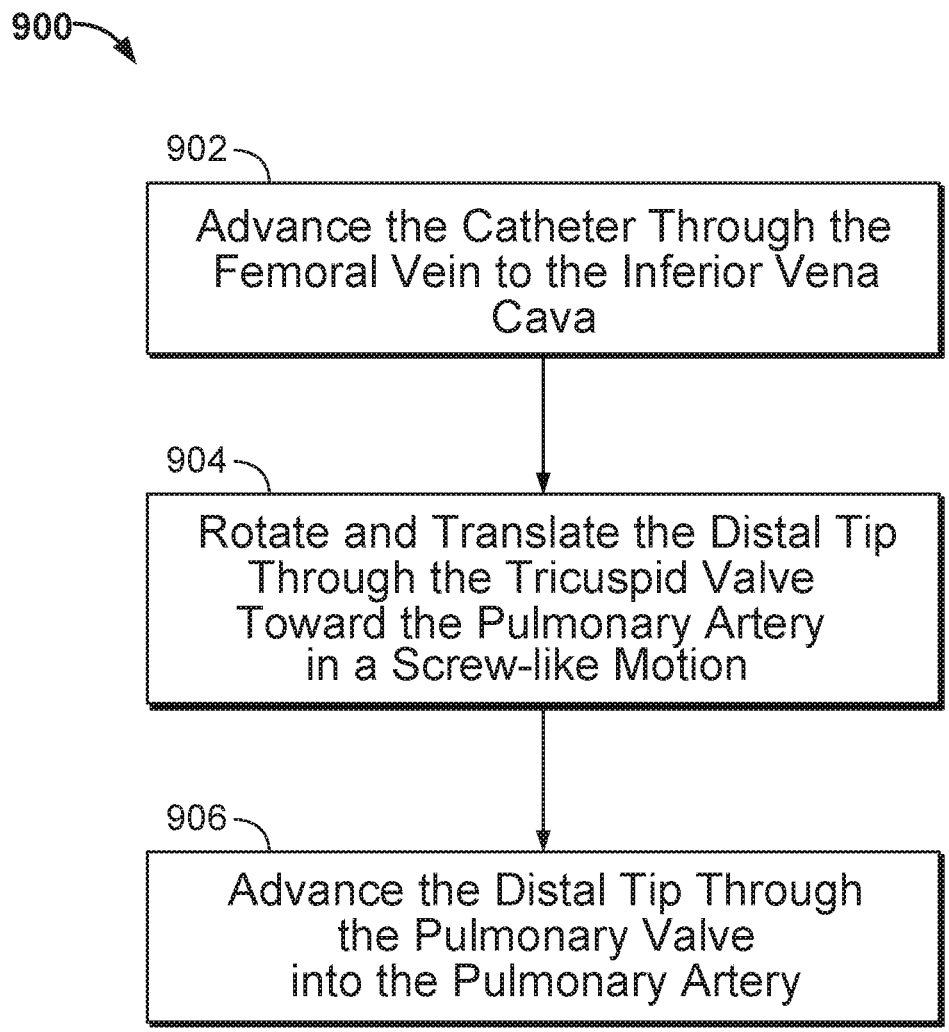
FIG. 9 shows an illustrative process for placing a cannula in a patient's right heart.

FIG. 9 shows an illustrative process 900 for placing a cannula in a patient's right heart. In step 902, the catheter (e.g., catheter 100 of FIG. 1, catheter 200 of FIG. 2A, or any other suitable catheter) is advanced through the femoral vein and through the patient's vasculature to the inferior vena cava. In some implementations, the catheter is introduced using an introducer sheath and/or a guidewire. In some implementations, the placement of the catheter is monitored by fluoroscopy or with the use of sensors incorporated into the catheter. The catheter may be configured for short-term use, such as during an emergency procedure or in conjunction with an imaging procedure. In some implementations, the catheter is configured for long-term use as a fully implantable heart pump. The catheter may be used for long-term implantation in a patient (e.g., >1 hr, >3 hr, >6 hr, >12 hr, >24 hr, >2 days, >10 days, >20 days, >45 days, >60 days or any suitable duration).

Once the catheter has been advanced to the inferior vena cava, in step 904, the distal tip of the catheter is rotated and translated through the tricuspid valve toward the pulmonary artery in a screw-like motion. The catheter includes a cannula (e.g., cannula 112 in FIG. 1, cannula 212 in FIG. 2A, or any other suitable cannula), a portion of which is approximated by a helix. The helix approximating the cannula shape is matched to an average anatomy of the right heart including the tricuspid valve, right ventricle and pulmonary valve. The rotation of the cannula in the direction of the helix advances the distal tip of the cannula through the tricuspid valve and into the right ventricle, with the body of the cannula following along the path of the helix. The distal tip of the cannula may deviate from the helical path in order to facilitate the successful advancement of the cannula through the tricuspid valve toward the pulmonary artery. Once in the right ventricle, the screw-like rotation of the helical cannula leads to the positioning of the cannula with the distal tip pointing toward the pulmonary valve. In some implementations, a flexible projection (e.g., flexible projection 224 in FIG. 2A, flexible projection 524 in FIG. 5, or any other suitable flexible projection) is attached at the distal tip of the cannula. The flexible projection can mechanically extend the cannula and prevents traumatic contact between the cannula and the interior walls of the heart.

The distal tip of the cannula is advanced through the pulmonary valve and into the pulmonary artery in step 906. The cannula is thus positioned such that the cannula traverses the tricuspid valve, right ventricle, pulmonary valve and pulmonary artery. The inlet ports are positioned in the inferior vena cava, while the outflow ports are positioned above the pulmonary valve in the pulmonary artery. The cannula can then be used to provide an additional blood flow from the inferior vena cava to the pulmonary artery. In some implementations, a flow rate of 4 lpm or more is provided through the cannula within the right heart of a patient. In some implementations, a flow rate of 3 lpm, 3.5 lpm, 4 lpm, 4.5 lpm 5 lpm, 6 lpm or any other suitable flow rate is provided. In some implementations, the flow rate is chosen based on the needs of the patient.

The helically-shaped cannula mimics the interior anatomy of the right heart to facilitate advancement of the cannula into the heart and proper positioning to provide cardiac support in the right heart. The cannula can be positioned to span from the inferior vena cava, through the tricuspid valve, through the right ventricle and through the pulmonary valve to extend into the pulmonary artery. Blood may flow through the cannula from the inferior vena cava to the pulmonary artery where it exits the outlet ports of the cannula to join the blood flow in the pulmonary artery. The shape of the cannula facilitates the insertion process for health care professionals. The helical shape of the cannula reflects the average anatomy of a sample patient population such that the probability of proper placement and fit of the cannula within the right heart of a patient is improved. The cannula may further be composed of a stable material, since the shape allows the insertion of the cannula without the need for a flexible or bendable cannula. Cannulas with an increased stability enable the use of implantable or long-term use cannulas.

The foregoing is merely illustrative of the principles of the disclosure, and the apparatuses can be practiced by other than the described embodiments, which are presented for purposes of illustration and not of limitation.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

I claim:

1. A catheter configured for delivering an intravascular blood pump within a patient's vasculature, comprising:
    a catheter body having a distal end, a proximal end, and a first longitudinal axis;
    a pump assembly disposed at the distal end of the catheter body, the pump assembly having a distal end portion;
    a cannula coupled to the distal end portion of the pump assembly, the cannula comprising a proximal cannula portion having inlet ports, and a distal cannula portion having outlet ports, the distal cannula portion having a pre-formed shape that is approximately helical, with a curvature that mimics the curvature of an anatomical pathway that traverses the inferior vena cava, right atrium, tricuspid valve, right ventricle and pulmonary valve of the patient's heart such that when the distal cannula portion is positioned along the anatomical pathway, the inlet ports are positioned in the inferior vena cava and the outlet ports are positioned in the pulmonary artery;
    wherein the helical shape approximated by the distal cannula portion has a second axis parallel to and offset from the first longitudinal axis of the catheter body.

2. The catheter of claim 1, wherein a distal tip of the cannula is angled toward a center of the second axis.

3. The catheter of claim 2, wherein the helical shape approximated by the distal cannula portion has a radius between about 10 mm and 50 mm.

4. The catheter of claim 3, wherein the helical shape approximated by the distal cannula portion has a radius between about 20 mm and 40 mm.

5. The catheter of claim 4, wherein the helical shape approximated by the distal cannula portion has a radius of about 30 mm.

6. The catheter of claim 1, wherein the helical shape approximated by the distal cannula portion has a pitch between about 50 mm and 140 mm.

7. The catheter of claim 6, wherein the helical shape approximated by the distal cannula portion has a pitch between about 70 mm and 120 mm.

8. The catheter of claim 7, wherein the helical shape approximated by the distal cannula portion has a pitch of about 90 mm.

9. The catheter of claim 1, wherein the helical shape approximated by the distal cannula portion completes one turn.

10. The catheter of claim 1, wherein a length of the distal cannula portion is about two-thirds of a total length of the cannula.

11. The catheter of claim 1, wherein the cannula has a total length of about 17 cm.

12. The catheter of claim 1, wherein the cannula in configured to extend through the tricuspid valve and the pulmonary valve into the inferior vena cava when positioned in the right heart.

13. The catheter of claim 1, wherein the cannula is configured to be approximately perpendicular to a plane defined by the tricuspid valve during entry through the right atrium into the right ventricle.

14. The catheter of claim 1, wherein the curvature of the distal end of the cannula is configured such that a distal tip of the cannula points toward the pulmonary valve after passing through the tricuspid valve.

15. The catheter of claim 1, wherein the helical shape of the cannula is configured to match an average patient anatomy of the right atrium, tricuspid valve, right ventricle, pulmonary valve and pulmonary artery during placement in the right heart.

16. The catheter of claim 1, wherein the cannula is sized for percutaneous delivery.

17. The catheter of claim 13, wherein the cannula has a diameter of about 10 Fr.

18. The catheter of claim 1, further comprising a flexible extension coupled to the distal cannula portion.

19. The catheter of claim 1, wherein the catheter is configured for percutaneous insertion into a patient through the anatomical pathway.

* * * * *

UNITED STATES PATENT AND TRADEMARK OFFICE
CERTIFICATE OF CORRECTION

PATENT NO.           : 10,722,625 B2                                  Page 1 of 1
APPLICATION NO.      : 15/156570
DATED                : July 28, 2020
INVENTOR(S)          : Christopher Zarins It is certified that error appears in the above-identified patent and that said Letters Patent is hereby corrected as shown below:

In the Specification

Column 2, Lines 9-10 - Delete "PCT/US/2011037984," and insert --PCT/US2011/037984,-- therefor.

Column 3, Line 39 - Delete "insertion." and insert --insertion;-- therefor.

Column 5, Line 23 - After "of", insert --a--.

Column 5, Line 43 - Delete "12," and insert --12-- therefor.

Column 6, Line 55 - Delete "(lpm 0" and insert --(lpm)-- therefor.

Column 7, Line 62 - Delete "432 *a-c*" and insert --432*a-c*-- therefor.

Column 8, Line 24 - Delete "634 *a-c*" and insert --634*a-c*-- therefor.

In the Claims

Column 12, Line 38 - In Claim 12, delete "in" and insert --is-- therefor.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*